(12) United States Patent
Hainze

(10) Patent No.: US 11,974,869 B2
(45) Date of Patent: May 7, 2024

(54) PORTABLE X-RAY CASSETTE POSITIONING SYSTEM AND METHOD

(71) Applicant: Kurt Hainze, Gardnerville, NV (US)

(72) Inventor: Kurt Hainze, Gardnerville, NV (US)

(*) Notice: Subject to any disclaimer, the term of this patent is extended or adjusted under 35 U.S.C. 154(b) by 38 days.

(21) Appl. No.: 17/583,961

(22) Filed: Jan. 25, 2022

(65) Prior Publication Data

US 2023/0233165 A1    Jul. 27, 2023

(51) Int. Cl.
    *A61B 6/00*    (2006.01)
    *A61B 6/04*    (2006.01)
    *A61B 6/42*    (2024.01)

(52) U.S. Cl.
    CPC .......... *A61B 6/4283* (2013.01); *A61B 6/4405* (2013.01); *A61B 6/0407* (2013.01)

(58) Field of Classification Search
    None
    See application file for complete search history.

(56) References Cited

U.S. PATENT DOCUMENTS

| | | | | |
|---|---|---|---|---|
| 3,443,093 A * | 5/1969 | Pierson | ................... | G03C 3/003 206/455 |
| 3,551,673 A * | 12/1970 | Siegel | ..................... | G03C 3/003 206/455 |
| 3,741,386 A * | 6/1973 | Schmidt | ................. | B65D 85/62 378/173 |
| 3,829,699 A * | 8/1974 | Anspach, Jr. | ............ | G03C 3/00 378/204 |
| 3,843,041 A * | 10/1974 | Oliverius | ................. | G03C 3/00 383/7 |
| 3,958,693 A * | 5/1976 | Greene | .................. | G03C 3/003 206/524.8 |
| 4,057,731 A * | 11/1977 | Loseff | ..................... | G21F 5/015 378/167 |
| 4,194,622 A * | 3/1980 | Lewis | .................... | A61B 50/30 422/26 |
| 4,759,643 A * | 7/1988 | Canno | .................... | B65D 27/16 383/88 |
| 4,902,543 A * | 2/1990 | Ernst | ...................... | G03C 3/003 428/36.1 |
| 4,913,288 A * | 4/1990 | Tanaka | ................. | G03B 42/042 206/455 |
| 5,045,708 A * | 9/1991 | Cooper | .................... | A61N 5/10 250/517.1 |
| 5,077,779 A * | 12/1991 | Steinhausen, Jr. | ..... | G03C 3/003 378/167 |
| 5,100,713 A * | 3/1992 | Homma | ............... | D03D 13/002 428/113 |

(Continued)

*Primary Examiner* — David P Porta
*Assistant Examiner* — Djura Malevic
(74) *Attorney, Agent, or Firm* — Mark A. Goodman, Esq.

(57) ABSTRACT

A system and method for the placement of a portable x-ray cassette is disclosed herein. In some embodiments, the system comprises a planar cassette element, a fabric, a collar element and a rigid sheet. The planar cassette element includes a hollow cavity disposed on a leading edge thereof and the fabric is configured to dispense from the hollow cavity, surround the planar cassette element and slide about the planar cassette element away from and toward the leading edge of the cassette element. The system allows for easy positioning of the portable x-ray cassette underneath a patient to be x-rayed.

8 Claims, 14 Drawing Sheets

(56) References Cited

U.S. PATENT DOCUMENTS

| | | | | |
|---|---|---|---|---|
| 5,102,234 A * | 4/1992 | Levy | B65D 31/12 | 383/38 |
| 5,123,535 A * | 6/1992 | Patnode | A61B 50/30 | 383/7 |
| 5,145,734 A * | 9/1992 | Ito | E04C 5/073 | 442/187 |
| 5,178,278 A * | 1/1993 | Oliverius | B65D 31/04 | 206/455 |
| 5,185,776 A * | 2/1993 | Townsend | G03B 42/04 | 378/204 |
| 5,247,182 A * | 9/1993 | Servant | G21F 3/02 | 250/516.1 |
| 5,377,254 A * | 12/1994 | Walling | G03B 42/04 | 378/204 |
| 5,407,277 A * | 4/1995 | Burke | B65D 31/12 | 206/459.1 |
| 5,441,251 A * | 8/1995 | Ohta | G03B 42/02 | 378/188 |
| 5,464,096 A * | 11/1995 | Hurwitz | B08B 1/00 | 206/812 |
| 5,466,561 A * | 11/1995 | Rantanen | G03B 42/042 | 378/182 |
| 5,576,552 A * | 11/1996 | Rantanen | G03C 3/003 | 250/581 |
| 5,712,486 A * | 1/1998 | Soltani | G03B 42/04 | 378/184 |
| 5,773,839 A * | 6/1998 | Krepel | G03G 15/758 | 250/580 |
| 5,783,278 A * | 7/1998 | Nishimura | D03D 49/22 | 428/102 |
| 5,788,377 A * | 8/1998 | Vetter | B65D 27/16 | 383/93 |
| 5,884,766 A * | 3/1999 | Marou | G03C 3/00 | 206/455 |
| 5,924,571 A * | 7/1999 | Cornelissen | B65D 5/0254 | 378/188 |
| 6,046,458 A * | 4/2000 | Rantanen | G03C 3/00 | 250/485.1 |
| 6,315,444 B1 * | 11/2001 | Koren | A61B 6/14 | 378/168 |
| 6,406,674 B1 * | 6/2002 | Bourne | A61B 90/92 | 206/439 |
| 6,612,310 B2 * | 9/2003 | Sklar | A61B 46/10 | 128/853 |
| 6,674,087 B2 * | 1/2004 | Cadwalader | G21F 1/106 | 128/849 |
| 6,742,928 B2 * | 6/2004 | Halpert | G03B 42/042 | 378/168 |
| 6,827,214 B2 * | 12/2004 | Alzner | G03C 3/003 | 206/455 |
| 7,505,555 B2 * | 3/2009 | Hermann | A61B 6/502 | 378/210 |
| 7,514,697 B2 * | 4/2009 | Schindlbeck | G21K 4/00 | 428/102 |
| 7,632,013 B1 * | 12/2009 | Bueltmann | G03B 42/04 | 378/204 |
| 7,700,922 B2 * | 4/2010 | Kuwabara | G01T 7/00 | 343/916 |
| 7,972,059 B2 * | 7/2011 | Behle | A61B 6/4283 | 378/182 |
| 8,157,443 B2 * | 4/2012 | Khan | G03C 3/00 | 378/165 |
| 8,237,127 B2 * | 8/2012 | Yoshida | G03B 42/04 | 378/182 |
| 8,350,241 B2 * | 1/2013 | Bustamante Grant | A61B 6/107 | 250/516.1 |
| 8,389,961 B2 * | 3/2013 | Yanagita | G03B 42/02 | 250/584 |
| 8,545,098 B2 * | 10/2013 | Behle | A61B 6/4423 | 378/182 |
| D715,939 S * | 10/2014 | Philipps | D24/158 | |
| 9,643,756 B2 * | 5/2017 | Tanaike | B65D 33/20 | |
| 9,668,709 B2 * | 6/2017 | Cardin | A61B 6/425 | |
| 9,702,986 B2 * | 7/2017 | Peters | G01T 1/2006 | |
| 9,864,078 B2 * | 1/2018 | Sumi | G03B 42/04 | |
| 10,464,728 B2 * | 11/2019 | Cruz | B32B 1/02 | |
| 10,675,111 B2 * | 6/2020 | Goy | A61B 6/107 | |
| 10,729,507 B2 * | 8/2020 | Beale | A61B 46/40 | |
| 11,439,360 B2 * | 9/2022 | DeYoung | A61B 46/20 | |
| 11,540,964 B2 * | 1/2023 | Borgman | A61G 7/05769 | |
| 11,577,910 B2 * | 2/2023 | Ayers | B65F 1/1623 | |
| 2001/0045319 A1 | 11/2001 | Kemper | A61B 7/02 | 181/131 |
| 2002/0060300 A1 * | 5/2002 | O'kane, Sr. | G21F 5/015 | 250/515.1 |
| 2002/0130272 A1 * | 9/2002 | Sauvage | G21K 4/00 | 250/483.1 |
| 2003/0021383 A1 * | 1/2003 | Masson | A61B 6/0421 | 378/177 |
| 2003/0077408 A1 * | 4/2003 | Haskin | A61B 50/00 | 428/40.1 |
| 2003/0112925 A1 * | 6/2003 | Wang | G03B 42/025 | 378/182 |
| 2003/0118156 A1 * | 6/2003 | Stahl | G03B 42/04 | 378/182 |
| 2003/0128815 A1 * | 7/2003 | Stahl | G03B 42/04 | 378/169 |
| 2004/0013322 A1 * | 1/2004 | Taylor | B65D 33/20 | 383/207 |
| 2005/0100251 A1 * | 5/2005 | Havens | B65D 81/052 | 383/107 |
| 2005/0226388 A1 * | 10/2005 | Reid | G03B 42/025 | 378/167 |
| 2005/0278991 A1 * | 12/2005 | Araujo | B65D 33/20 | 40/6 |
| 2006/0150987 A1 * | 7/2006 | Dillon | A61B 46/00 | 128/853 |
| 2006/0204398 A1 * | 9/2006 | Bales | A61L 2/18 | 422/28 |
| 2007/0255248 A1 * | 11/2007 | Hendren | A61F 15/001 | 604/385.02 |
| 2007/0272873 A1 * | 11/2007 | Jadrich | G01T 1/20 | 250/370.11 |
| 2008/0159486 A1 * | 7/2008 | Hesl | A61B 6/4464 | 378/189 |
| 2008/0292060 A1 * | 11/2008 | Leblans | G21K 4/00 | 378/167 |
| 2009/0136003 A1 * | 5/2009 | Gestetner | A61B 6/4423 | 378/189 |
| 2009/0316861 A1 * | 12/2009 | Behle | G03B 42/04 | 378/182 |
| 2010/0072097 A1 * | 3/2010 | Khan | G03C 3/00 | 206/455 |
| 2010/0111263 A1 * | 5/2010 | Lamberty | A61B 6/4283 | 378/189 |
| 2010/0171052 A1 * | 7/2010 | Thoms | H04N 1/04 | 250/584 |
| 2010/0308238 A1 * | 12/2010 | Bustamante Grant | G21F 3/02 | 250/515.1 |
| 2011/0069817 A1 * | 3/2011 | Behle | A61B 6/4423 | 378/177 |
| 2012/0199753 A1 * | 8/2012 | Chuang | G01V 5/0008 | 250/390.04 |
| 2022/0218295 A1 * | 7/2022 | Foster | A61B 6/107 | |

* cited by examiner

PORTABLE X-RAY CASSETTE POSITIONING SYSTEM AND METHOD

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of radiography of existing art and more specifically relates to a portable x-ray cassette having means to greatly reduce effort in positioning the portable x-ray cassette underneath a patient.

RELATED ART

Since portable x-ray machines were developed and portable exams have been performed, there has existed considerable difficulty in positioning a portable x-ray cassette underneath a patient. Many factors contribute to the challenge; for example, patient size, bedding adjuncts (cooling blankets, waffle mattresses), type of material the mattress surface is made of, whether the patient is surrounded by equipment (resulting in limited access and confined working space), etc. The difficulty can be of such a nature and degree that injuries to medical staff, such as x-ray technicians or other assistants, have resulted. Injuries to back, muscle strains, wrist or shoulder trauma, etc. have all contributed to unnecessary time-off costs, and even chronic problems for the medical staff member.

The principle culprit is typically the amount of friction between the bedding and the portable x-ray cassette that inhibits the attempt to position the portable x-ray cassette underneath the patient. Efforts have been made to solve this problem; however, these attempts have not been satisfactory as they either do not address the underlying problem and do not make a sufficient difference.

For a more detailed description of some of the challenges related to this subject matter, reference is made the following professional journal articles, which are hereby incorporated herein by reference: Loose R. "*A better way to perform portable x-rays*". Radiol Manage. 2011 January-February; 33(1):30-6; quiz 37-8. PMID: 21366144, and Meittunen E, Graham K, Spence D. "*Evaluation of a hidden occupational healthcare risk: the portable X-ray.*" Radiol Manage. 2004 November-December; 26(6):44-50, 52-3. PMID: 15633510.

Considering the foregoing, a more suitable solution in the art is desired.

SUMMARY OF THE INVENTION

In view of the foregoing disadvantages inherent in the known radiography art, the present disclosure provides a novel portable x-ray cassette positioning system. The general purpose of the present disclosure, which will be described subsequently in greater detail, is to provide a system that allows for the greatly reduced effort in placement of a portable x-ray cassette underneath a patient to be x-rayed.

A system for the placement of a portable x-ray cassette is disclosed herein. The system includes a planar cassette element, a collar, and a fabric. The cassette element includes a hollow cavity disposed along a leading edge thereof. The fabric may be configured to dispense from the hollow cavity and surround the cassette element. Further, the fabric may be configured to slide about the cassette element away from and toward the leading edge of the cassette element.

According to another embodiment, a method of positioning a portable x-ray cassette for a bedbound patient is also disclosed herein. The method includes providing the system as above; dispensing the fabric from the leading edge of the cassette element; folding the fabric about the cassette element; wedging the leading edge of the cassette element underneath the bedbound patient; and pushing the cassette element under the bedbound patient such that the fabric dispenses further about the cassette element as the cassette element passes further underneath the bedbound patient, thereby decreasing the friction between the cassette element and the bedbound patient.

According to another embodiment, a system for the placement of a portable x-ray cassette may include a fabric dispensing element and a fabric. The fabric dispensing element may be configured to attach to and remove from the portable x-ray cassette and may include a hollow cavity configured to hold the fabric. The fabric may be configured to dispense from the hollow cavity and surround the portable x-ray cassette. Further, the fabric may be configured to slide about the portable x-ray cassette away from and toward a leading edge thereof.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a portable x-ray cassette positioning system and method, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to a portable x-ray cassette and more particularly to a portable x-ray cassette having means for easily positioning the portable x-ray cassette underneath a patient to be x-rayed. Generally, the portable x-ray cassette may include a low friction material that exits from a front of the portable x-ray cassette and surrounds the portable x-ray cassette as it is pushed underneath the patient. The low friction material may be dispensed at the same rate that the portable x-ray cassette is advanced toward the underneath of the patient, acting as a low friction fabric tunnel through which the portable x-ray cassette is pushed and thereby causing low friction movement of the portable x-ray cassette. Thus, it does not matter what the friction coefficient of bedding and/or adjuncts may be.

Figure 1A:
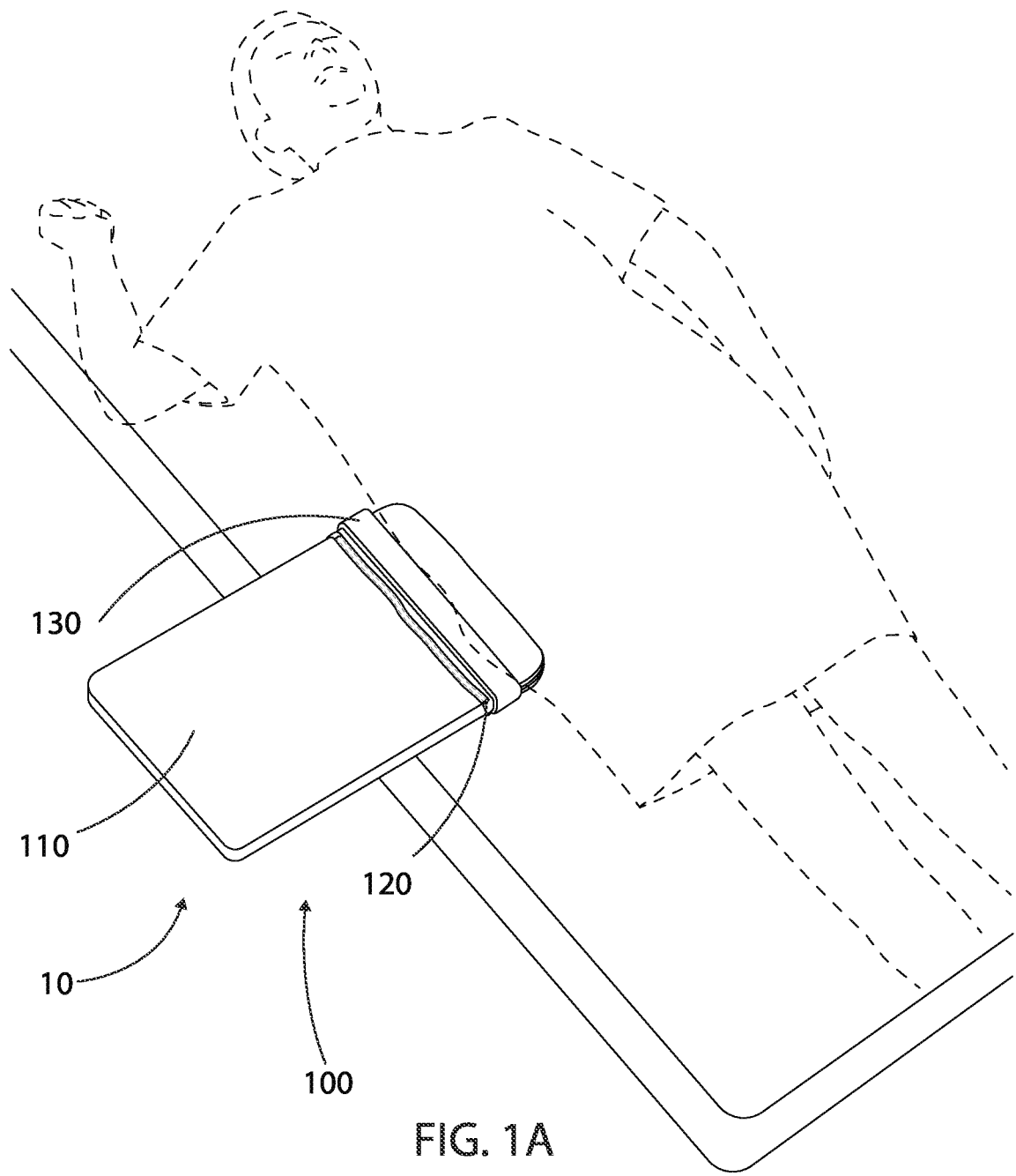
FIG. 1A is a top perspective view of a system being used for the placement of a portable x-ray cassette underneath a bedbound patient, according to an embodiment of the disclosure.
Figure 1B:
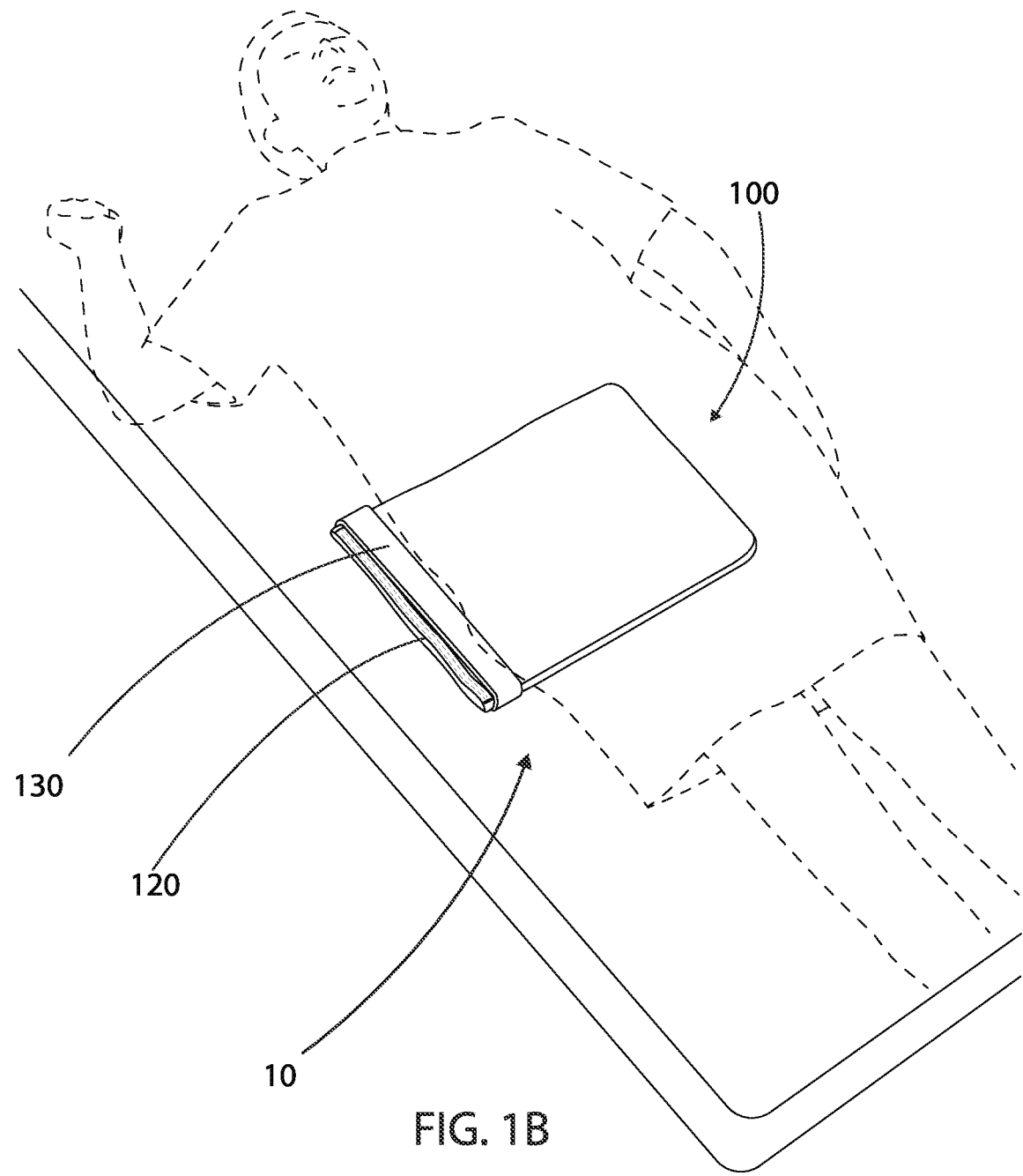
FIG. 1B is a top perspective view of the portable x-ray cassette placed underneath the bedbound patient, according to an embodiment of the disclosure.
Figure 2:
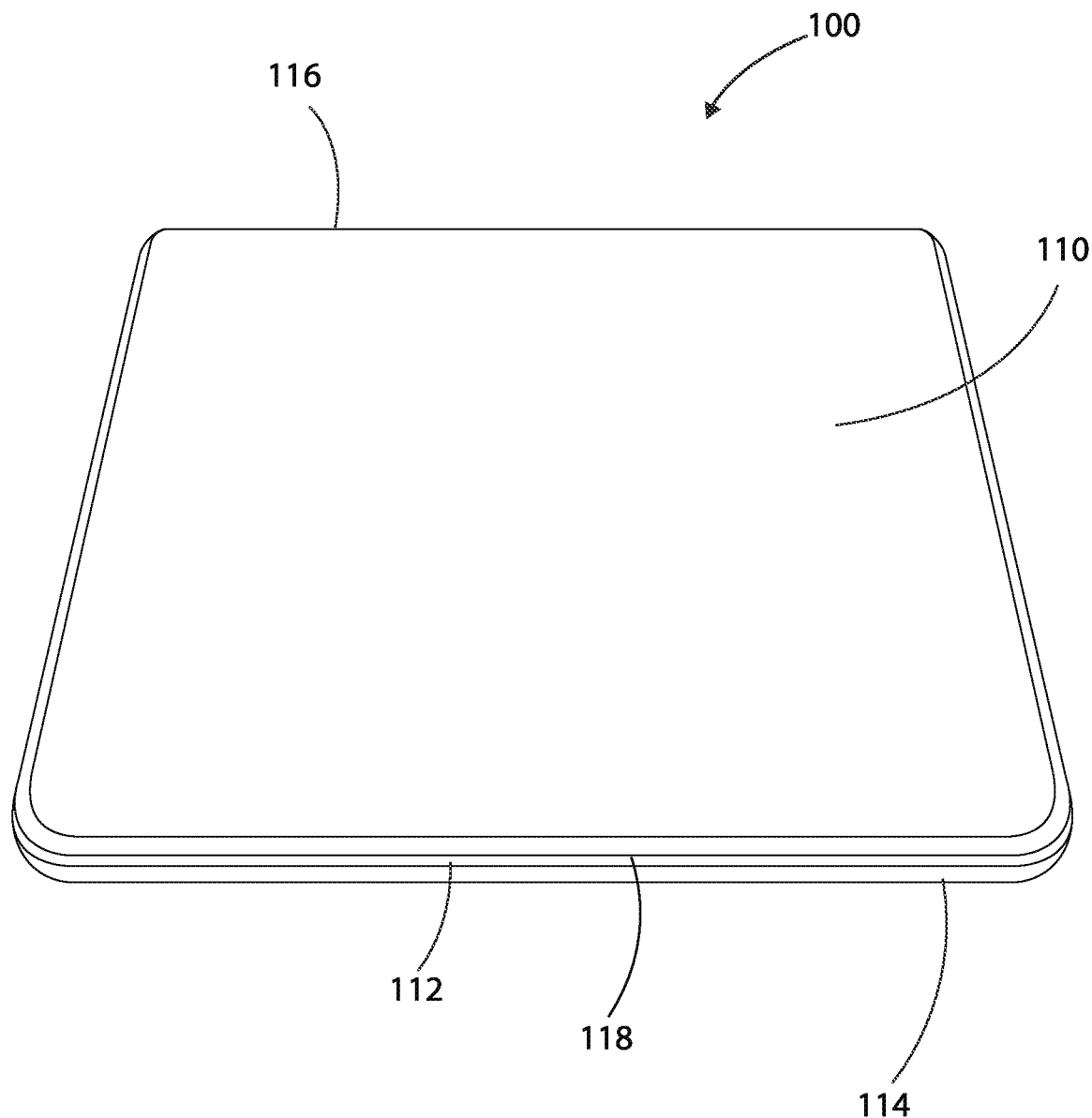
FIG. 2 is a front perspective view of a planar cassette element having a hollow cavity and a narrow opening, according to an embodiment of the present disclosure.
Figure 3:
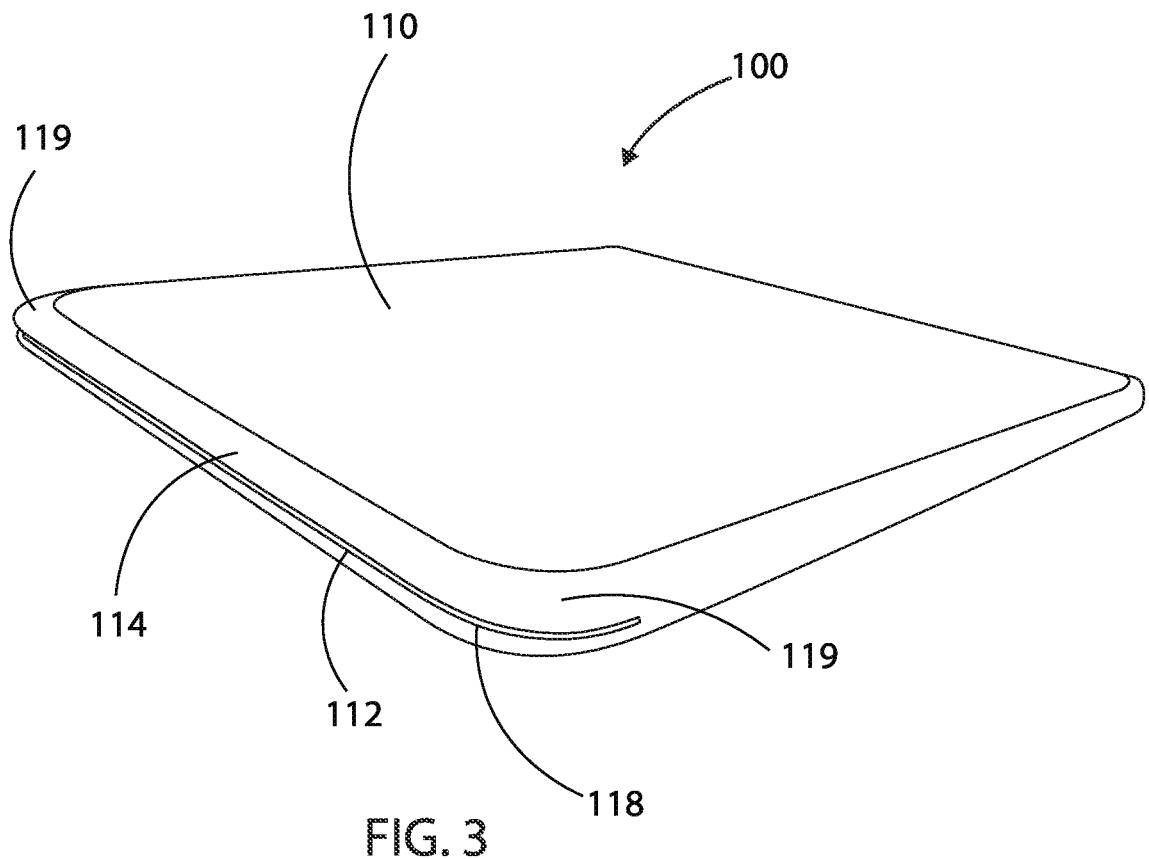
FIG. 3 is a side perspective view of the planar cassette element having the hollow cavity and the narrow opening, according to an embodiment of the present disclosure.

Referring now more specifically to the drawings by numerals of reference, FIGS. 1A-13 show a system 100 according to an embodiment of the present disclosure. As shown in FIGS. 1A-1B the system 100 may be used for the placement of a portable x-ray cassette 10. Particularly, the system 100 may be used for placing and positioning the portable x-ray cassette 10 under a bedbound patient (shown in these figures in broken lines). In some embodiments, the system may comprise a planar cassette element 110 and a fabric 120.

Figure 4:
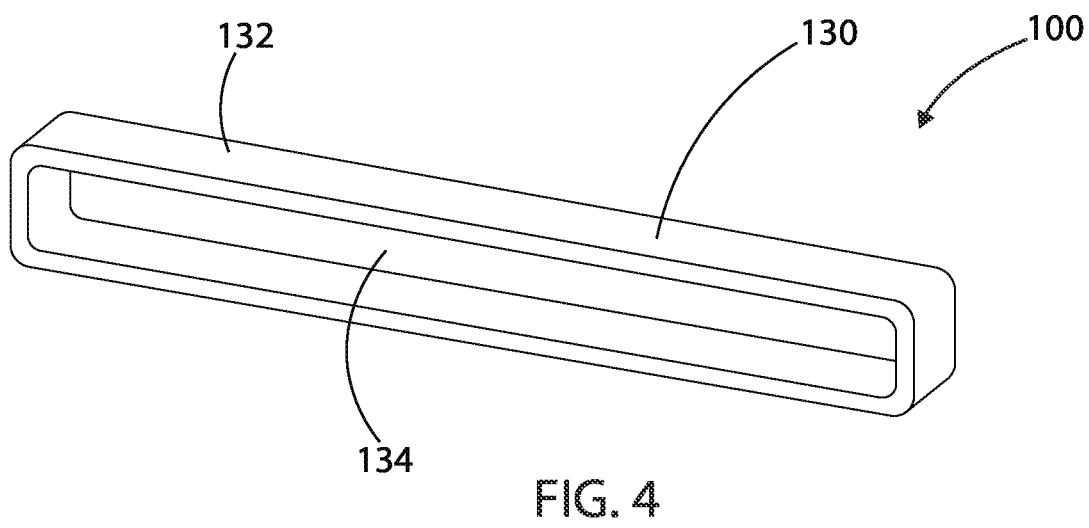
FIG. 4 is a front perspective view of a collar element, according to an embodiment of the present disclosure.
Figure 5:
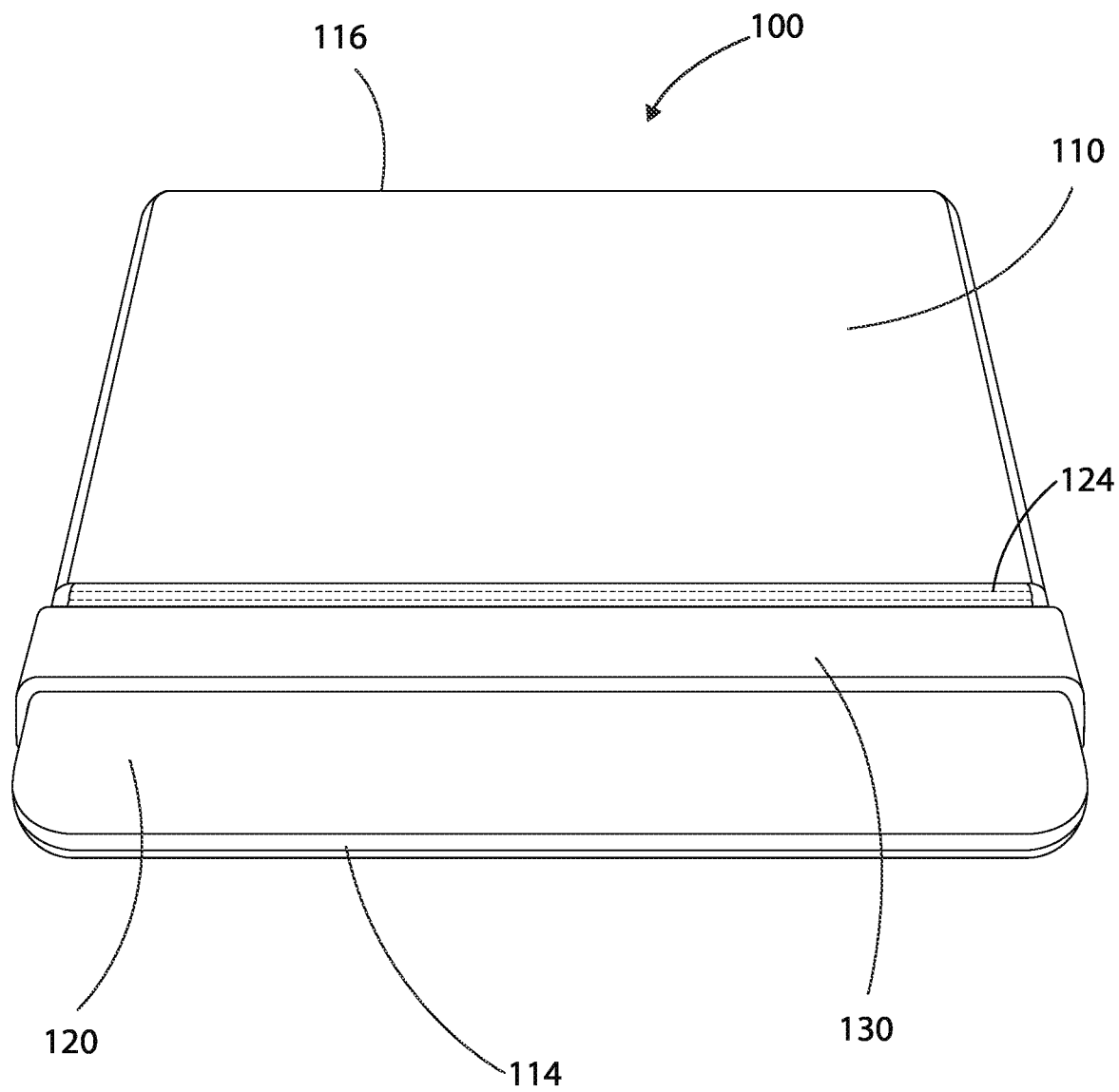
FIG. 5 is a front perspective view of the system and illustrating the planar cassette element with a fabric being dispensed from the hollow cavity, and a collar element, according to an embodiment of the present disclosure.
Figure 6:
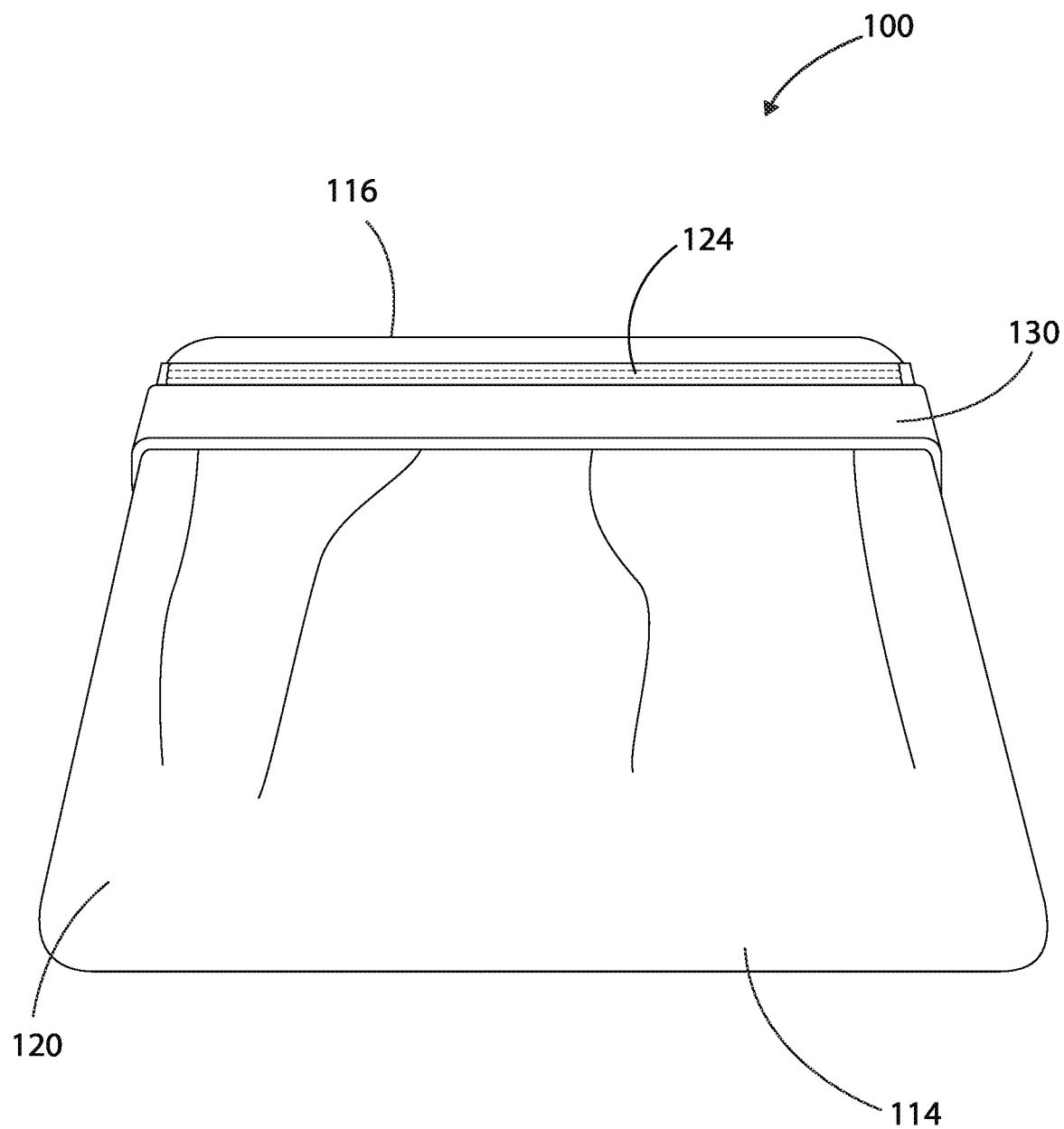
FIG. 6 is a front perspective view of the system and illustrating the fabric surrounding the planar cassette element, according to an embodiment of the present disclosure

Referring more specifically to FIGS. 2-11 illustrating the planar cassette element 110, the fabric 120 and a collar element 130. As shown specifically in FIGS. 2-3, the planar cassette element 110 may include rounded corners 119 and a hollow cavity 112 disposed along a leading edge 114 of the planar cassette element 110. The hollow cavity 112 being accessible via a narrow opening 118 disposed along an entirety of the leading edge 114. The fabric 120 may be held within the hollow cavity 112. As shown in FIGS. 5-6 particularly, the fabric 120 may be configured to dispense from the hollow cavity 112 (via the narrow opening 118 [FIG. 3]) and surround the planar cassette element 110. In some embodiments, an edge 122 of the fabric 120 may be attached inside the hollow cavity 112. This may allow the fabric 120 to dispense from the hollow cavity 112 and surround the planar cassette element 110 whilst the edge 122 remains attached within the hollow cavity 112, enabling easy replacement of the fabric 120 therewithin. This may be a permanent attachment or a temporary attachment. When temporary, the fabric 120 may be removed from the hollow cavity 112. This may aid in cleaning of the fabric 120.

Figure 7:
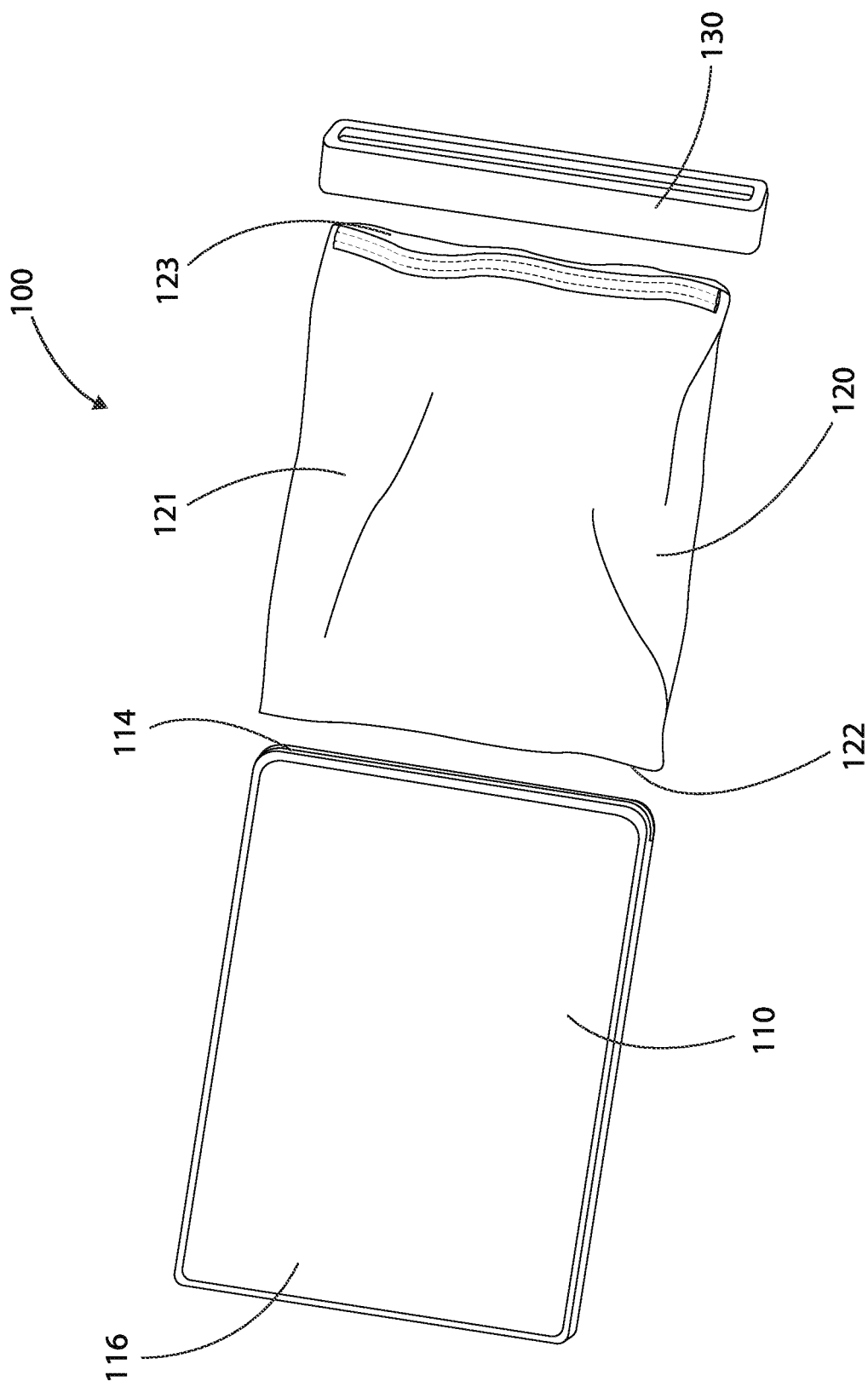
FIG. 7 is an exploded view of the system illustrating order of assembly of the planar cassette element, the fabric and the collar element.
Figure 8:
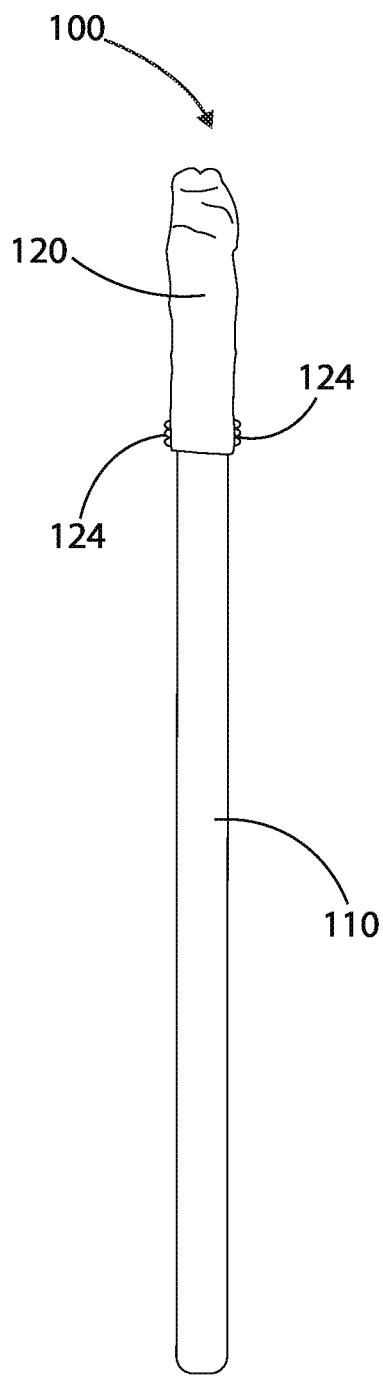
FIG. 8 is a side view of the system illustrating the fabric surrounding the planar cassette element.
Figure 9:
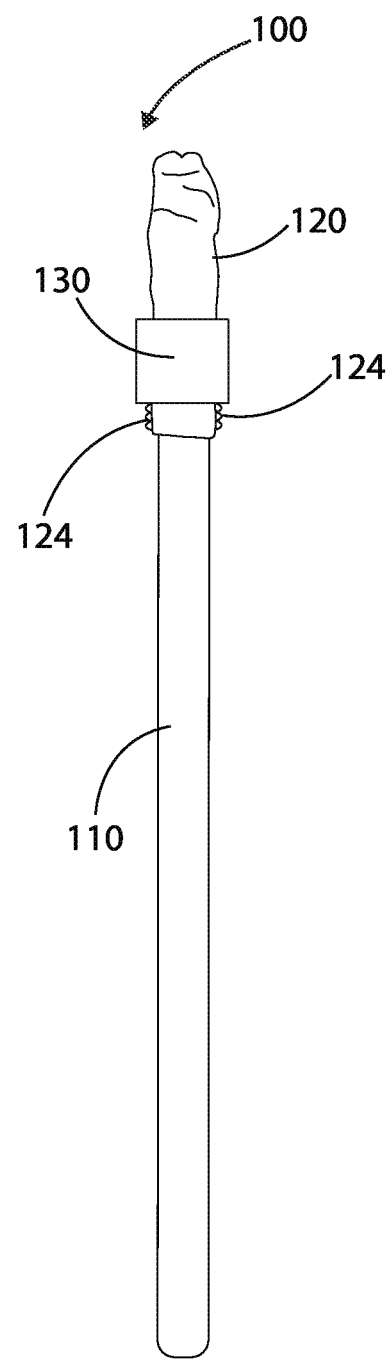
FIG. 9 is a side view of the system illustrating the collar element surrounding the planar cassette element and the fabric.
Figure 10:
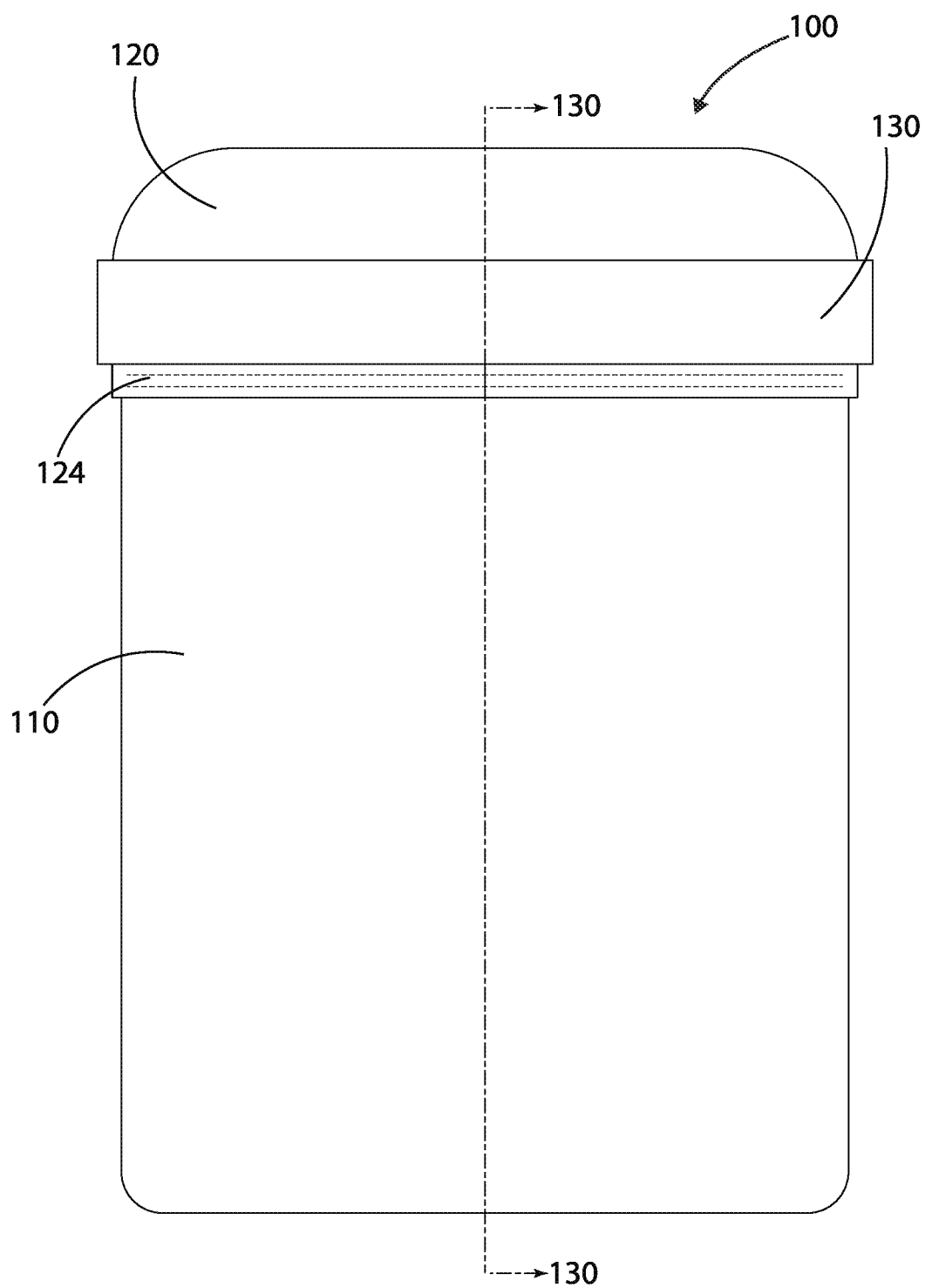
FIG. 10 is a top view of the system illustrating the collar element surrounding the planar cassette element and the fabric.
Figure 11:
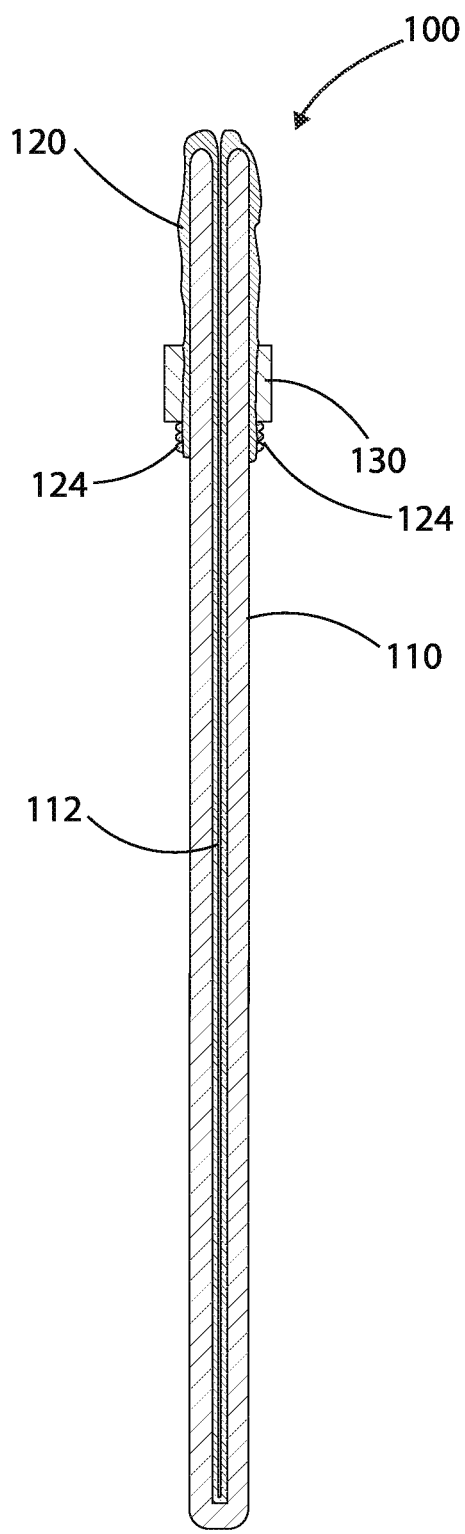
FIG. 11 is a cross-sectional view of the system taken from line 11-11 in FIG. 10, illustrating the collar element surrounding the planar cassette element and the fabric.

As shown in FIG. 7, when flattened and smoothed, the fabric may include a shape equal (or at least substantially equal) to that of the planar cassette element 110. Further, in some embodiments, the fabric 120 may include the shape/configuration of a bag-like enclosure. For example, the fabric 120 may be configured to encase the planar cassette element 110 in a similar fashion as to how a pillowcase encases a pillow. As such, in this example and as shown in FIG. 7, the fabric 120 may define a casing 121 having an open mouth 123 and the edge 122 of the fabric may be closed. For example, the edge 122 may be sewn closed. When the edge 122 of the fabric 120 is attached inside the hollow cavity 112, the open mouth 123 may be folded over the leading edge 114 of the planar cassette element 110 (as shown in FIG. 5 specifically). Preferably, two ridges 124 of thick material may be sewn onto the fabric about the open mouth 123.

As demonstrated in FIGS. 5-6, the fabric 120 may be configured to slide about the planar cassette element 110 away from and toward the leading edge 114 thereof. In use, the open mouth 123 of the fabric 120 may slide over the planar cassette element 110, thereby surrounding the planar cassette element 110 and fully encasing it when the open mouth 123 reaches a following edge 116 of the planar cassette element 110 (the following edge 116 being opposite the leading edge 114). As such, the fabric 120 may preferably comprise a low friction fabric. For example, the low friction fabric may comprise nylon, silk, vinyl, neoprene, polyester, polytetrafluoroethylene, Parafricta, or the like. However, it should be appreciated that this list of materials is not exhaustive.

To facilitate sliding of the fabric 120, the system 100 may further comprise the collar element 130. As shown in FIG. 4, the collar element 130 may include an outer frame 132 defining an opening 134. The collar element 130 may be configured to surround the planar cassette element 110 and the fabric 120. For example, as shown in FIGS. 5-6 and FIGS. 9-11, the collar element 130 is attached about the leading edge 114 of the planar cassette element 110 (atop the fabric 120) when the open mouth 123 is folded over the leading edge 114 of the planar cassette element 110 (the planar cassette element 110 and the fabric 120 received within the opening 134 of the collar element 130). The collar element 130 may be configured to facilitate even dispersal of the fabric 120 about the planar cassette element 110.

The collar element 130 may be slid onto the fabric 120 until it comes into contact with the two ridges 124 of thick material located about the open mouth 123 of the fabric 120. The two ridges 124 may be too thick to pass under the collar element 130, and thus, the collar element 130 may grip and pull the fabric 120 via the two ridges 124. As such, when the planar cassette element 110 is pushed towards the bedbound patient (after being initially positioned where the bedbound patient's body meets a bed on which they are lying [FIG. 1A]), the movement may cause the collar element 130 to pull the fabric 120 further out of the hollow cavity 112 allowing it to encase the planar cassette element 110 and creating a low friction fabric 'tunnel' through which the planar cassette element 110 moves. As such, the planar cassette element 110 slides only within the fabric 120 and does not contact mattress, bedding material, the bedbound patient and/or other materials/objects surrounding the patient. Only the fabric 120 contacts the mattress, bedding material, the bedbound patient and/or other materials/objects surrounding the patient and due to the low friction fabric, there is minimal to no friction when placing the planar cassette element 110 underneath the bedbound patient.

Figure 12:
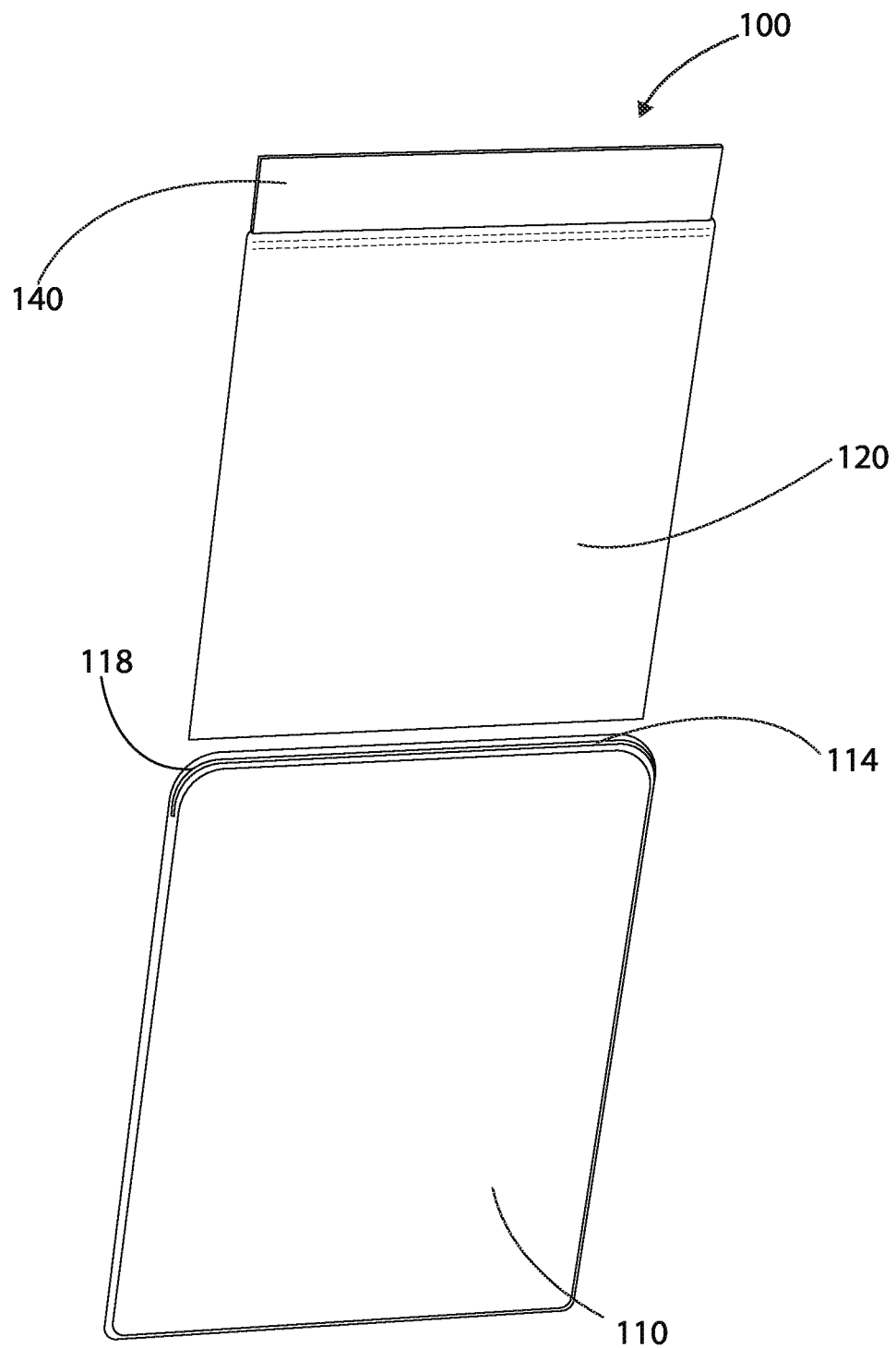
FIG. 12 is a top perspective view of a rigid sheet being used to insert the fabric into the hollow cavity of the planar cassette element, according to an embodiment of the present disclosure.
Figure 13:
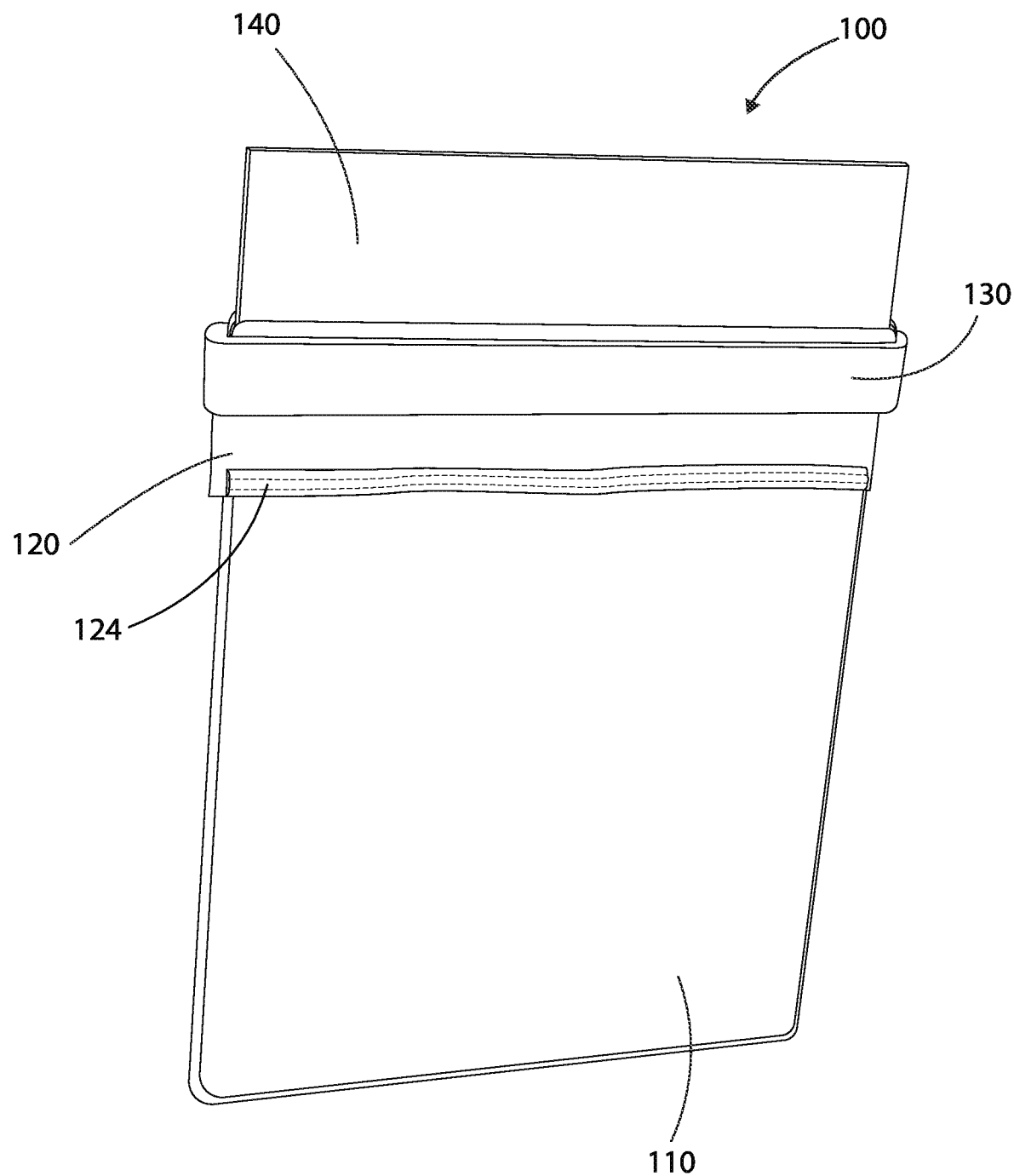
FIG. 13 is a top perspective view of the rigid sheet having inserted the fabric into the hollow cavity of the planar cassette element, according to an embodiment of the present disclosure.

Referring now specifically to FIGS. 12-13, in some embodiments, to aid in the replacement of the fabric 120 back within the hollow cavity 112, a rigid sheet 140 may be provided. The rigid sheet 140 may be configured to insert the fabric 120 into the hollow cavity 112. As shown, the rigid sheet 140 may include a length and width substantially equal to a length and width of the hollow cavity 112. To place the fabric 120 into the hollow cavity 112, the rigid sheet 140 may be slid into the open mouth 123 of the fabric 120 until it meets the edge 122 thereof, providing rigidity to the fabric 120. The fabric 120 and the rigid sheet 140 may then be inserted into the narrow opening 118 in the leading edge 114 of the planar cassette element 110 and pushed into the hollow cavity 112. Once the fabric 120 (and the rigid sheet 140) are fully inserted within the hollow cavity 112, the rigid sheet 140 may be withdrawn, thereby leaving the fabric 120 in operational readiness within the hollow cavity 112. As above, the open mouth 123 may then be folded over the leading edge 114 of the planar cassette element 110.

In addition to this, the rigid sheet 140 may be used for inserting the fabric 120 back into the hollow cavity 112 after use when the fabric 120 has not been fully removed from the hollow cavity 112.

Figure 14:
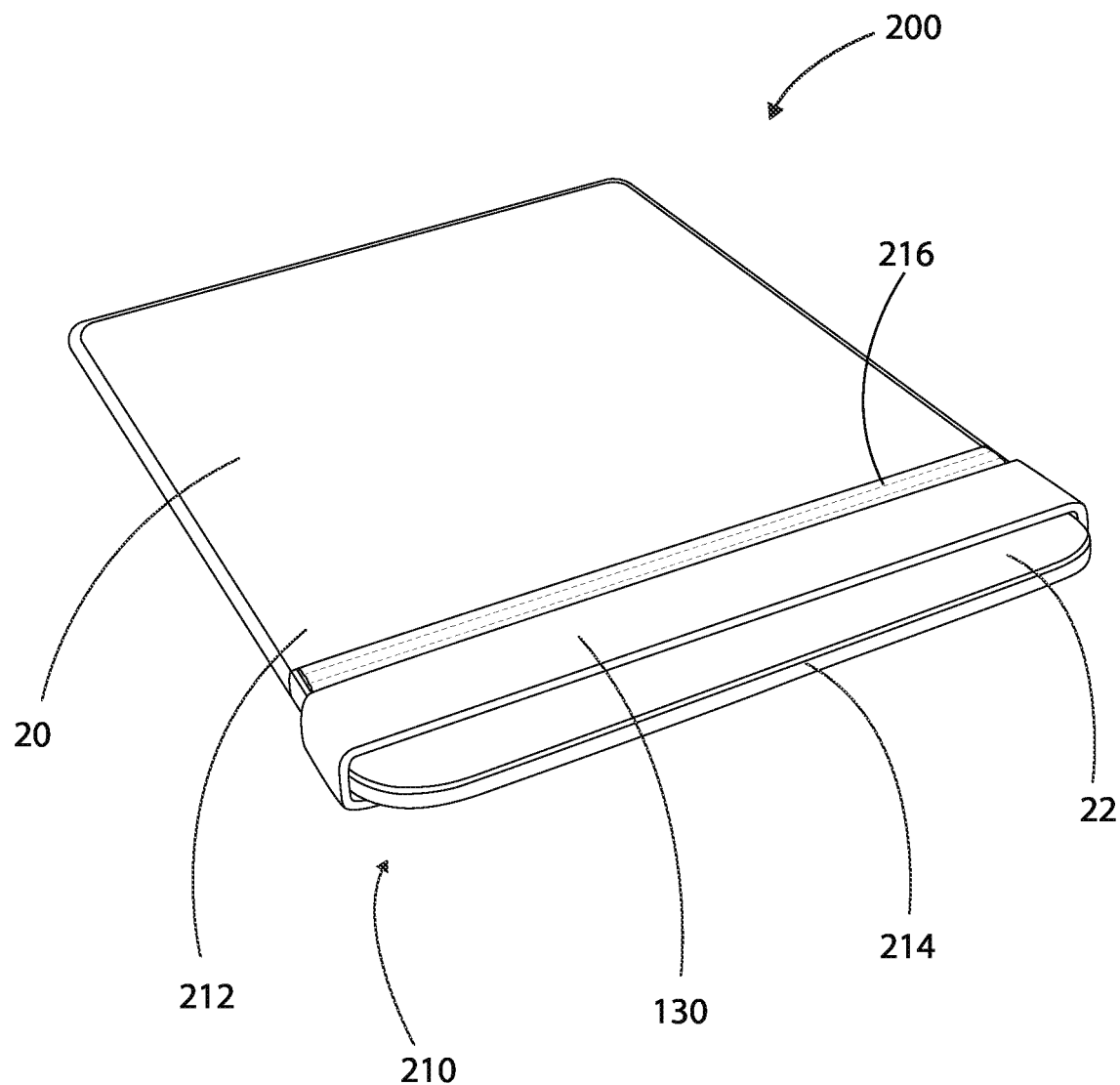
FIG. 14 is a front perspective view of a system having a fabric dispensing element, a fabric and a collar element, according to an embodiment of the present disclosure.

Referring now specifically to FIG. 14 there is shown a system 200 according to another embodiment of the present disclosure. The system 200 may include one or more components or features of the system 100 as described above and may be used for the placement of a portable x-ray cassette 20. In this embodiment, the system 200 may be auxiliary to the portable x-ray cassette 20. For example, in this embodiment, the system 200 may comprise a fabric dispensing element 210 configured to attach to and remove from the portable x-ray cassette 20.

The fabric dispensing element 210 may comprise a fabric 212 (similar or same as the fabric 120 discussed above) and a hollow cavity 214 configured to hold the fabric 212. Similar to the embodiment discussed above, the fabric 212 may be configured to dispense from the hollow cavity 214 and surround the portable x-ray cassette 20, and further configured to slide about the portable x-ray cassette 20 away from and toward a leading edge 22 thereof. As shown in FIG. 14, the fabric 212 may also include two ridges 216 of thick material. Further, the system 200 may comprise a collar element 230 (similar or same as the collar element 130 discussed above) configured to surround the portable x-ray cassette 20 and the fabric 212 and facilitate the even dispersal of the fabric 212 about the portable x-ray cassette 20. The system 200 may further comprise other similar elements to the system 100 discussed above, such as the rigid sheet 140 (FIGS. 12-13).

Figure 15:
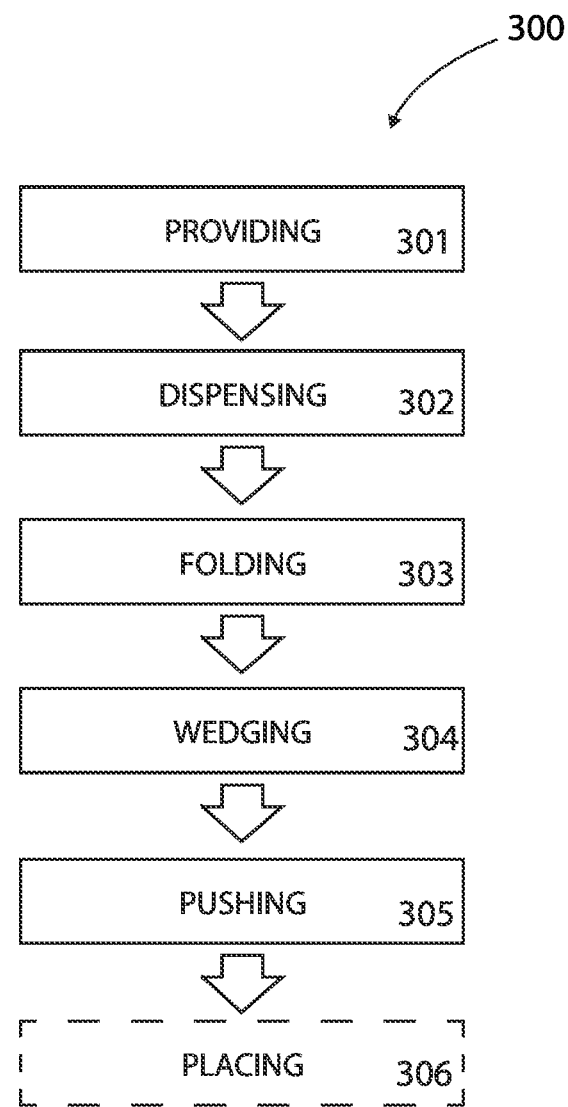
FIG. 15 is a flow diagram illustrating a method of positioning a portable x-ray cassette for a bedbound patient, according to an embodiment of the present disclosure.

Referring now to FIG. 15 showing a flow diagram illustrating a method 300 of positioning a portable x-ray cassette for a bedbound patient, according to an embodiment of the present disclosure. In particular, the method 300 may include one or more components or features of the system 100 as described above. As illustrated, the method 300 may include the steps of: step one 301, providing the system 100 as above; step two 302, dispensing the fabric from the leading edge of the planar cassette element; step three 303, folding the fabric about the planar cassette element; step four 304, wedging the leading edge of the planar cassette element underneath the bedbound patient; and step five 305, pushing the planar cassette element toward the bedbound patient such that the fabric dispenses further about the cassette element as the cassette element passes further underneath the bedbound patient, thereby decreasing the friction between the cassette element and the bedbound patient. Further steps may include step six 306, placing collar element about the cassette element and the fabric, the collar element configured to surround the cassette element and the fabric to facilitate the even dispersal of the fabric about the cassette element as the cassette element is pushed underneath the bedbound patient.

It should be noted that certain steps are optional and may not be implemented in all cases. Optional steps of method 300 are illustrated using dotted lines in FIG. 15 so as to distinguish them from the other steps of method 300. It should also be noted that the steps described in the method of use can be carried out in many different orders according to user preference. The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other methods for positioning a portable x-ray cassette for a bedbound patient are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

The numbered list format used in the claims of the application is used solely for organizational purposes to provide clarity thereto and is not meant to limit in any way the claimed matter nor any aspect of the present disclosure.

What is claimed is:

1. A system for the placement of a portable x-ray cassette comprising:
   a. a planar cassette element having a hollow cavity disposed along a leading edge of the planar cassette element;
   b. a fabric housed within the hollow cavity of the planar cassette element, the fabric being configured to dispense from the hollow cavity of the planar cassette element and surround the planar cassette element;

c. the fabric is configured to pull out from the hollow cavity and then fold over the planar cassette element about the leading edge of the planar cassette element; and d. a collar element configured to surround the planar cassette element and the fabric, the collar element is further configured to facilitate the even dispersal of the fabric about the planar cassette element.

2. The system of claim 1, further comprising two ridges of material sewn onto the fabric, wherein the collar element is configured to grip and pull the fabric via the two ridges.

3. The system of claim 1, wherein an edge of the fabric is attached inside the hollow cavity.

4. The system of claim 1, wherein the fabric comprises a low friction fabric, the low friction fabric selected from the group consisting of nylon, silk, vinyl, neoprene, polyester, polytetrafluoroethylene, and Parafricta.

5. The system of claim 1, further including a rigid sheet, the rigid sheet is configured to insert the fabric into the hollow cavity.

6. The system of claim 1, wherein the fabric has the shape of a pillowcase.

7. A method of positioning a portable x-ray cassette for a bedbound patient, the method comprising the steps of:

a. providing a planar cassette element according to claim 1;

b. dispensing the fabric from the leading edge of the planar cassette element;

c. folding the fabric about the planar cassette element;

d. wedging the leading edge of the planar cassette element underneath the bedbound patient;

e. pushing the planar cassette element toward the bedbound patient such that the fabric dispenses further about the planar cassette element as the planar cassette element passes further underneath the bedbound patient, thereby decreasing the friction between the planar cassette element and the bedbound patient.

8. The method of claim 7, further comprising the step of placing collar element about the planar cassette element and the fabric, the collar element is configured to surround the planar cassette element and the fabric to facilitate an even dispersal of the fabric about the planar cassette element as the planar cassette element is pushed underneath the bedbound patient.

* * * * *